(12) United States Patent
Miyamoto

(10) Patent No.: US 10,178,943 B2
(45) Date of Patent: Jan. 15, 2019

(54) MEDICAL DRIVE DEVICE

(71) Applicant: FUJIFILM Corporation, Tokyo (JP)

(72) Inventor: Manabu Miyamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/499,367

(22) Filed: Apr. 27, 2017

(65) Prior Publication Data

US 2017/0224196 A1 Aug. 10, 2017

Related U.S. Application Data

(63) Continuation of application No. 14/039,551, filed on Sep. 27, 2013, now Pat. No. 9,668,640.

(30) Foreign Application Priority Data

Sep. 28, 2012 (JP) .................................. 2012-217291

(51) Int. Cl.
*A61B 1/00* (2006.01)
*A61B 1/31* (2006.01)
*A61B 17/00* (2006.01)

(52) U.S. Cl.
CPC ........ *A61B 1/00133* (2013.01); *A61B 1/0014* (2013.01); *A61B 1/0016* (2013.01); *A61B 1/00045* (2013.01); *A61B 1/00135* (2013.01); *A61B 1/00156* (2013.01); *A61B 1/31* (2013.01); *A61B 2017/00398* (2013.01); *F04C 2270/041* (2013.01)

(58) Field of Classification Search
CPC .................... A61B 1/00133; A61B 1/00156
See application file for complete search history.

(56) References Cited

U.S. PATENT DOCUMENTS

| | | | |
|---|---|---|---|
| 2,651,734 A | 9/1953 | Field | |
| 2,669,669 A | 2/1954 | Spaulding | |
| 3,177,481 A | 4/1965 | Joy et al. | |
| 4,493,643 A | 1/1985 | Tachibana | |
| 4,917,096 A | 4/1990 | Englehart et al. | |
| 5,804,936 A | 9/1998 | Brodsky et al. | |
| 5,951,581 A | 9/1999 | Saadat et al. | |
| 2001/0031975 A1 | 10/2001 | Whitman et al. | |
| 2006/0187573 A1 | 8/2006 | Slye | |
| 2007/0038026 A1 | 2/2007 | Yoshida et al. | |
| 2008/0086029 A1 | 4/2008 | Uchiyama et al. | |
| 2008/0200759 A1 | 8/2008 | Niwa et al. | |
| 2009/0233747 A1 | 9/2009 | Sheridan et al. | |
| 2011/0065988 A1 | 3/2011 | Eidenschink et al. | |

FOREIGN PATENT DOCUMENTS

| | | |
|---|---|---|
| JP | 2008-93029 A | 4/2008 |
| WO | WO 2009/114137 A2 | 9/2009 |

*Primary Examiner* — Timothy J Neal
*Assistant Examiner* — Aaron B Fairchild
(74) *Attorney, Agent, or Firm* — Birch, Stewart, Kolasch & Birch, LLP

(57) ABSTRACT

An object is to detect the pressing force of a tip driven unit. In the controller 22, a motor control circuit 85, a load change detection unit 86, a moving speed calculation unit 87 that calculates the moving speed of a rotating body 41, a pressing force detection unit 88 that obtains the pressing force of the rotating body 41 based on the moving speed which is calculated, a CPU 89, and an alarm 91 are disposed. The pressing force is obtained based on the cycle of load change by the joint 41a in which a front end and a rear end overlap with each other is formed in the rotating body 41.

16 Claims, 13 Drawing Sheets

MEDICAL DRIVE DEVICE

This application is a Continuation of copending application Ser. No. 14/039,551, filed on Sep. 27, 2013, which claims priority under 35 U.S.C. § 119(a) to Application No. 2012-217291, filed in Japan on Sep. 28, 2012, all of which are hereby expressly incorporated by reference into the present application.

BACKGROUND OF THE INVENTION

1. Field of the Invention

The present invention relates to a medical drive device that is attached to a medical apparatus to move a tip side of the medical apparatus.

2. Description of the Related Art

In the medical field, endoscopes are in wide use for the observation of the inner parts of specimens. Such an endoscope includes an operation unit, and an insertion unit that is inserted into the specimen. An imaging element such as a CCD is accommodated in a tip portion of the insertion unit, and an image captured by the imaging element is displayed on a monitor.

To deal with the difficulties of the endoscope insertion operation, an endoscope driving device that assists the insertion (propulsion) of the endoscope which has a tip driven unit driven by a motor and attached to the tip side of the endoscope by moving the tip driven unit is known. For example, WO2009/114137A2 discloses an endoscope propulsion auxiliary device in which a bag-shaped rotating body (toroid) is used as the tip driven unit and the rotating body is pinched and moved in a circulating manner by a driving wheel driving the motor and a driven roller. The rotating body rotates in contact with an inner wall of the digestive tract, such as the colon, of the specimen, for example, a human body, and the tip side of the endoscope moves forward into the digestive tract.

Also, JP2008-093029A discloses a self-propelled rotation-type endoscope system in which a rotating housing that is formed of a metallic plate member wound in a spiral shape to have flexibility is attached in a rotatable manner to the insertion unit of the endoscope via a mouthpiece and the rotating body is rotated to move the insertion unit forward. The rotating housing rotates in contact with the inner wall of the digestive tract, and thus propelling force is given in the insertion direction to the insertion unit of the endoscope. In this manner, the insertion of the endoscope can be facilitated even in a highly curved digestive tract such as the colon.

In JP2008-093029A, load on the motor increases and the rotating speed decreases to decrease the propelling force of the rotating housing when the friction between the rotating housing and the inner wall of the digestive tract increases due to, for example, the strong pressing of the rotating housing against the inner wall of the digestive tract. In this case, propulsion by the rotating housing cannot be performed. Therefore, in a case where the rotating speed of the motor decreases, the current supplied to the motor is increased to make up for the decrease in the rotating speed by increasing the rotating speed of the motor. In this case, motor torque increases. The motor torque is detected by a motor driver, and a detected torque value is compared to a preset limit torque value. In a case where the detected torque value is larger than the limit torque value, the supply of the current to the motor is stopped to stop the driving of the motor while a warning is generated by a buzzer or a warning light to suppress the failure of the motor by the excess torque. Further, frequent stopping of the motor is prevented by varying the limit torque value.

Also, in JP2008-093029A, the rotating housing has flexibility so as to be deformed along with the deformation of a flexible tube of the endoscope and is configured of a long tube which has approximately the same length as the insertion unit of the endoscope. Therefore, there is a case where the torsion of the rotating housing itself causes the rotating speed of the tip portion to be lower than the rotating speed of a base end portion. Even in this case, the rotating speed of the motor increases and the motor torque increases.

SUMMARY OF THE INVENTION

In a case where the rotating housing is strongly pressed against the inner wall of the digestive tract, it is necessary to apply a torque limit. However, in JP2008-093029A, the same motor torque increase is detected in a case where the motor torque is increased by the strong pressing of the rotating housing against the inner wall of the digestive tract and in a case where the motor torque is increased by the torsion of the rotating housing and the friction loss is increased when the torque is transmitted to the tip portion by the curvedness of the flexible tube or the like, and thus it is impossible to determine which one causes the motor torque increase. Also, the torque of the spiral-shaped rotating housing is increased by not only the friction of itself but also the friction caused by a body fluid in which the rotating housing rotates. There is no distinction between the increase caused by the friction and the torque increase caused by the pressing. Therefore, there is a problem that the limit torque is applied even though it is not necessary to limit the torque.

An object of the present invention is to provide a medical drive device that can detect the strong pressing of the tip driven unit.

In order to achieve the above object, the medical drive device according to the present invention that has a driving unit which moves a tip driven unit by the driving of a motor includes a load generation unit that is formed in the tip driven unit to change a load during the movement, and a moving speed calculation unit that detects the timing of generation of load change by the load generation unit to calculate the moving speed of the tip driven unit.

Also, it is preferable that the present invention further include a pressing force detection unit that detects a pressing force of the tip driven unit based on the moving speed.

Also, it is preferable that the driving unit have a mounting tube that is mounted on a tip portion of an endoscope, a driving tube that is supported in a rotatable manner by the mounting tube, a support tube that is arranged on an outer circumference of the mounting tube, a driving wheel that is rotated by the driving tube, and a driven roller that is attached to the support tube. It is preferable that the tip driven unit be a rotating body that covers an inner circumferential surface and an outer circumferential surface of the support tube, be pinched between the driving wheel and the driven roller, and move in a circulating manner in the axial direction of the support tube.

Further, it is preferable that the rotating body surround the support tube with the sheet-shaped rotating body and be formed in a bag shape which has a joint by overlapping and bonding both end portions with each other, and the load generation unit be the joint.

Further, it is preferable that the load generation unit be a protruding portion or a recessed portion that is formed in the rotating body.

Also, it is preferable that the protruding portion or the recessed portion be formed over the entire circumference of the rotating body at a predetermined gap along the moving direction of the rotating body.

Further, it is preferable that the medical drive device further include a moving load reduction unit that reduces the moving load of the tip driven unit when the pressing force exceeds a predetermined value.

Also, it is preferable that the moving load reduction unit reduce the rotating speed of the motor.

Further, it is preferable that the medical drive device further include a display unit that displays the strength of the pressing force exceeding the predetermined value.

Also, it is preferable that the display unit be an alarm that generates a warning sound.

Further, it is preferable that the display unit be an alarm that generates a sound at an interval according to the strength of the pressing force.

Also, it is preferable that the display unit be a monitor that displays an endoscope image.

According to the present invention, the pressing force of the tip driven unit can be simply detected by measuring the moving speed of the tip driven unit. Also, the moving speed can be obtained with a simple structure since the load generation unit is formed in a pressed tip portion and the moving speed of the tip driven unit is calculated based on the timing of generation of the load change by the load generation unit.

DESCRIPTION OF THE PREFERRED EMBODIMENTS

First Embodiment

Figure 1:
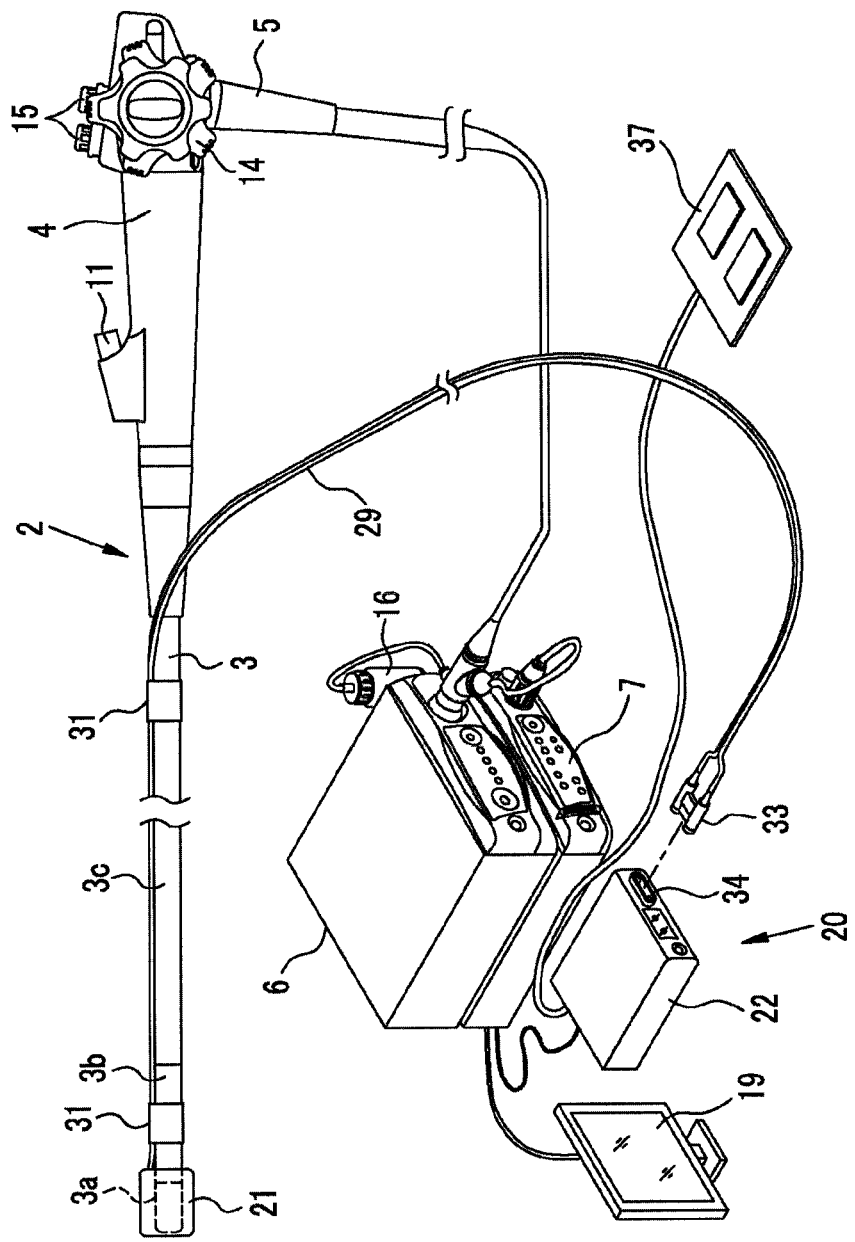
FIG. 1 is a schematic view of an endoscope system.
Figure 2:
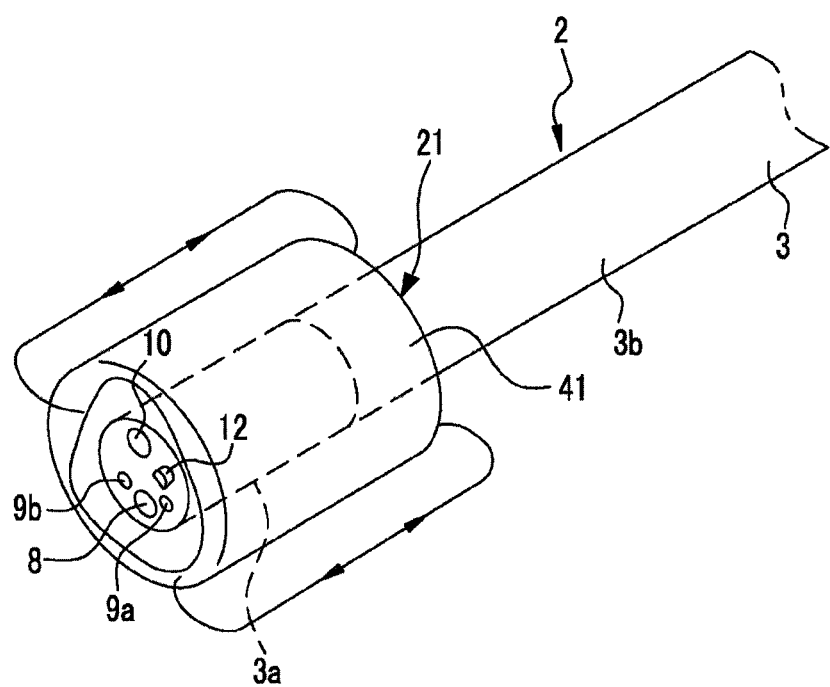
FIG. 2 is a perspective view showing a tip portion and a propulsion auxiliary unit of an endoscope.

As shown in FIG. 1 and FIG. 2, a medical endoscope 2 includes an insertion unit 3 that is inserted into a body cavity, for example, the digestive tract such as the colon, an operation unit 4 that is used to grip the endoscope 2 and operate the insertion unit 3, and a universal cord 5. The endoscope 2 is connected to a light source device 6 and a processor device 7 by the universal cord 5.

The insertion unit 3 has a hard tip portion 3a into which a solid-state image element, for example, a CCD image sensor, is built, a curved portion 3b that is continuously provided on a rear side of the tip portion 3a and is bendable in the up-down and left-right directions, and a flexible pipe unit 3c that is placed between the curved portion 3b and the operation unit 4.

In the tip portion 3a of the insertion unit 3, an imaging window 8, illumination windows 9a and 9b, and a forceps outlet 10 from which forceps tips project are disposed. The forceps outlet 10 communicates with a forceps inlet 11 that is disposed in the operation unit 4. Into the forceps inlet 11, various treatment tools whose tips are arranged with forceps, syringe needles, high-frequency scalpels, and the like are inserted. Also, in the tip portion 3a, an injection nozzle 12 that sprays air and rinse water toward the imaging window 8 is disposed.

The illumination windows 9a and 9b are arranged on both sides of the imaging window 8. The illumination windows 9a and 9b emit illumination light supplied from the light source device 6 toward a digestive tract observation site. Reflected light of the illumination light from the observation site is incident on the CCD image sensor arranged therebehind though the imaging window 8. An imaging signal by the CCD image sensor is sent to the processor device 7, undergoes image processing, and is displayed on a monitor 19.

In the operation unit 4, an angle knob 14 that bends the curved portion 3b in the up-down and left-right directions, and an operation button 15 that is operated when the air and the water are sent, suctioned, or the like are disposed. Also, the universal cord 5 is connected to the operation unit 4. As is known, an air-sending and water-sending tube, a signal cable, and a light guide are accommodated in the universal cord 5. The air-sending and water-sending tube is connected to an air-sending device and a water-sending tank 16. The signal cable connects the processor device 7 with an imaging unit that has the CCD, and transmits a control signal and an imaging signal. The light guide is connected to the light source device 6, and transmits the illumination light from the light source device 6 to the illumination windows 9a and 9b of the tip portion 3a.

An endoscope propulsion auxiliary device (medical drive device) 20 that propels (moves forward or backward) the insertion unit 3 in the digestive tract has a propulsion auxiliary unit 21 and a controller 22. The propulsion auxiliary unit 21 is attached in a removable manner to the tip portion 3a of the insertion unit 3. The propulsion auxiliary unit 21 is driven by a master motor 25 and a slave motor 26 (refer to FIG. 8). The motors 25 and 26 are respectively linked to a master wire 27 and a slave wire 28 (refer to FIG.

8) that transmits rotation torque for propelling the propulsion auxiliary unit 21. Each of the wires 27 and 28 is inserted into a flexible duplicate parallel sheath 29.

The sheath 29 is fixed to the insertion unit 3 of the endoscope 2 by a surgical tape 31. In this manner, while the endoscope 2 mounted with the propulsion auxiliary unit 21 is inserted into the body cavity, the sheath 29 is integrated with the insertion unit 3, and an unintentional behavior is not performed in the body cavity.

The controller 22 is connected to the processor device 7. A rear end of each of the wires 27 and 28 is attached to a bifurcated plug 33. Via the plug 33, each of the wires 27 and 28 is linked to a connector 34 of the controller 22.

The controller 22 is connected to an operation panel (not shown). The operation panel is disposed with a driving control button or the like for inputting instructions for forward movement, backward movement, and stopping of the propulsion auxiliary unit 21, and is operated by an operator (doctor).

A foot switch 37 is connected to the controller 22. A switch (not shown) disposed within the controller 22 is turned on and off by the operation of the foot switch 37 to switch between states where an internal circuit is connected and is not connected. The internal circuit enters the connection state when the foot switch 37 is operated, and enters the non-connection state when the foot switch 37 is not operated.

Figure 3:
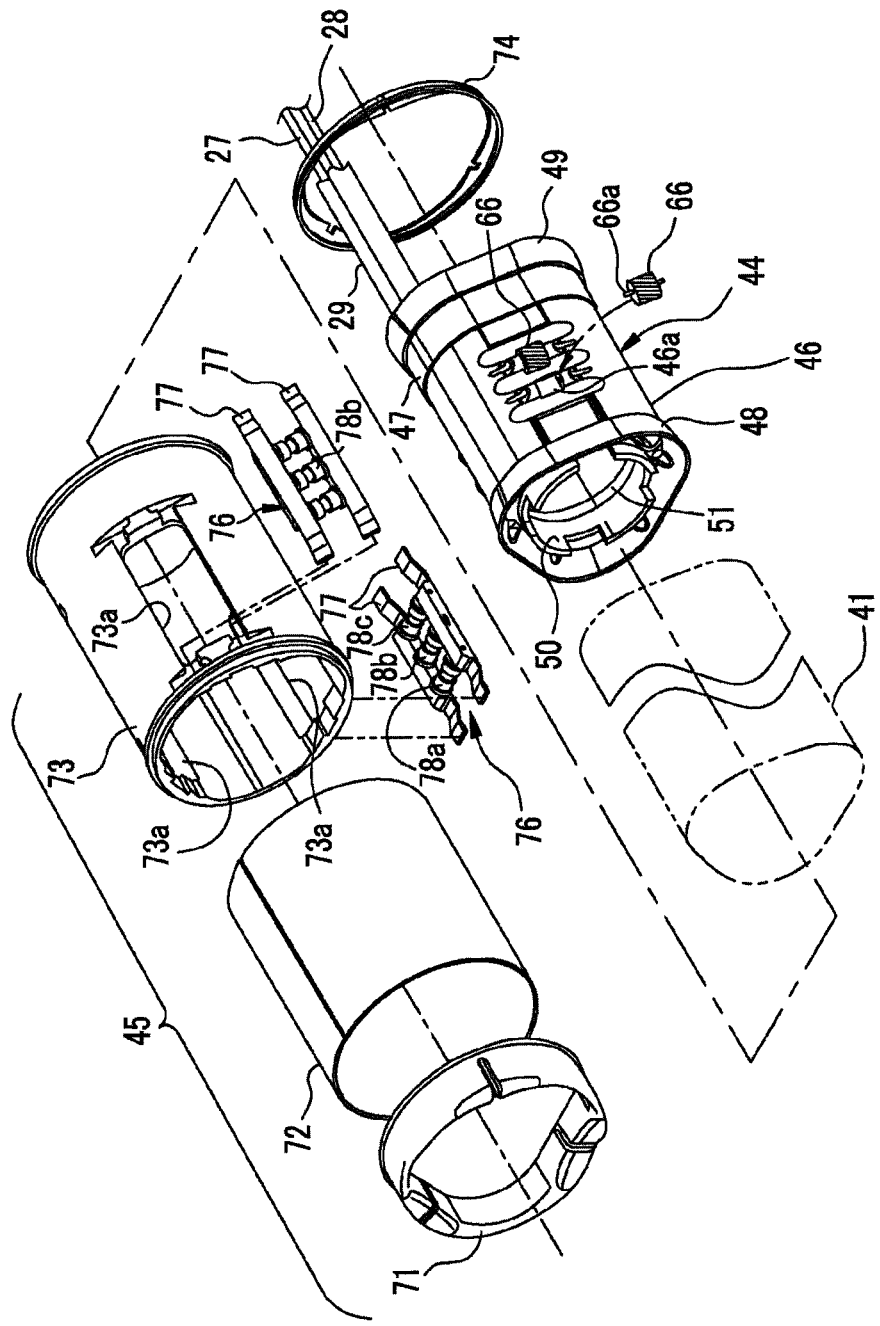
FIG. 3 is an exploded perspective view of the propulsion auxiliary unit.
Figure 4:
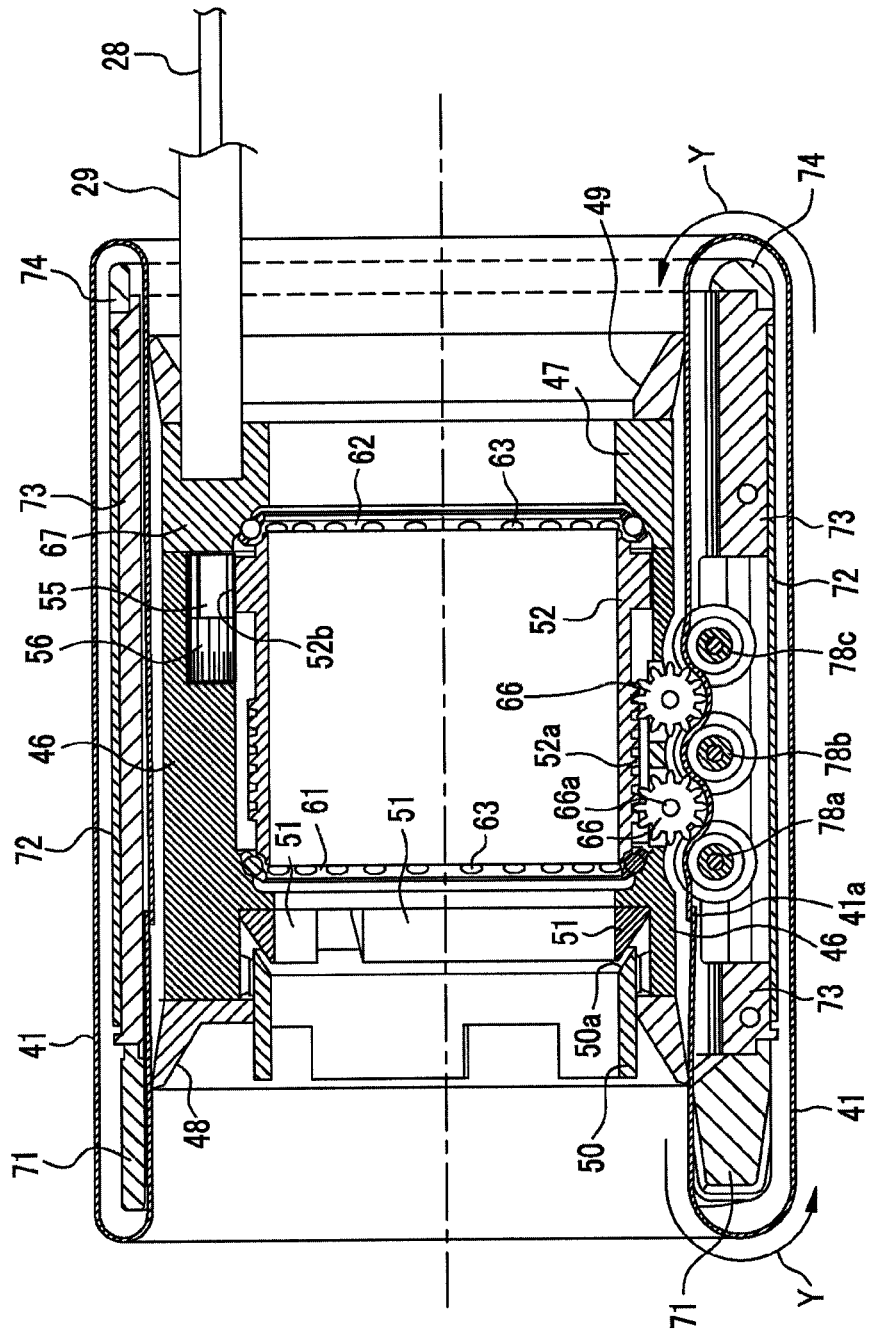
FIG. 4 is a cross-sectional view showing the propulsion auxiliary unit.
Figure 5:
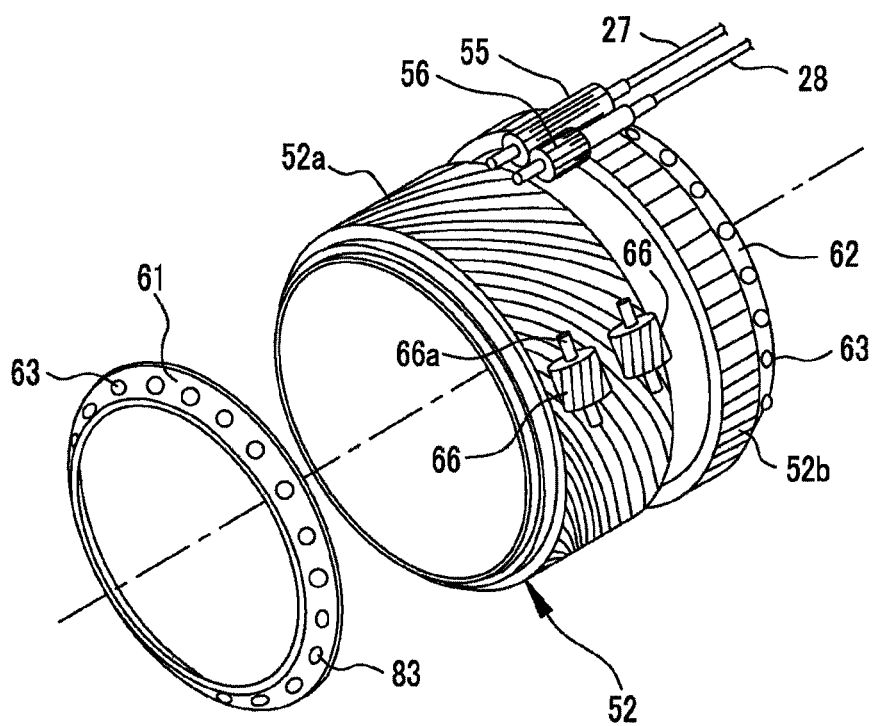
FIG. 5 is a perspective view showing a driving gear, a driving tube, a driving wheel, and a bearing ring.

As shown in FIG. 2, the propulsion auxiliary unit 21 of the endoscope propulsion auxiliary device 20 has a rotating body 41 (tip driven unit) that is in contact with an inner wall of the digestive tract and generates forward force and backward force on the insertion unit 3 of the endoscope 2. In the embodiment, the rotating body 41 has a bag shape called toroid or a doughnut shape, and moves in a circulating manner along the axis. For the rotating body 41, a material that has flexibility and elasticity is used, examples of which include biocompatible plastic such as polyvinyl chloride, polyamide resin, fluorine resin, urethane, and polyurethane. Also, the rotating body 41 is expressed as expanded in a tubular shape in FIG. 3 and FIG. 6 to facilitate the understanding of the structure, but the rotating body 41 has a toroidal bag body (refer to FIG. 2) in the final assembly form thereof.

As shown in FIGS. 3 to 6, the propulsion auxiliary unit 21 has an inner unit 44 that is a structure inside the rotating body 41 which is expanded in a tubular shape, and an outer unit 45 that is a structure outside the rotating body 41. The inner unit 44 has an approximately triangular-shaped mounting tube 46 that is attached to the insertion unit 3 of the endoscope 2, an approximately triangular tube-shaped cap 47 that is locked to a rear end side of the mounting tube 46 by press-fitting, and a front wiper 48 and a rear wiper 49 that are respectively fixed to a tip side of the mounting tube 46 and a rear end side of the cap 47. Also, the inner unit 44 has a clamper 50 that is screwed to a thread formed on a front end side inner circumference of the mounting tube 46 to move in the axial direction by rotation, a C ring 51 formed of a synthetic resin whose inner diameter and outer diameter increase or decrease according to the axial-direction movement of the clamper 50, and a cylindrical-shaped driving tube 52 that is supported on an inner circumference of the mounting tube 46 in a rotatable manner.

In a recessed portion formed on the rear end side of the cap 47, a tip of the sheath 29 is fixed by adhesion, heat welding, or the like. A tip portion of each of the wires 27 and 28 projecting from the tip of the sheath 29 projects forward from the cap 47 through a through-hole formed in the cap 47, and a master driving gear 55 and a slave driving gear 56 are fixed to the master wire 27 and the slave wire 28, respectively. From a tip of each of the driving gears 55 and 56, a shaft that is a rotation center projects, and the shafts are rotatably supported in such a manner as to be inserted into holes disposed in the mounting tube 46.

Both ends of the driving tube 52 are supported in a rotatable manner on an inner circumferential side of the mounting tube 46 via a front bearing ring 61 and a rear bearing ring 62. In each of the bearing rings 61 and 62, bearing balls 63 are arranged in an annular shape. The driving tube 52 is stopped by the cap 47 fixed to a rear end of the mounting tube 46. On an outer circumferential surface of the driving tube 52, a worm gear 52a and a spur gear 52b are disposed. The spur gear 52b is formed in a rear end portion of the driving tube 52, and is fitted into the master driving gear 55.

The slave driving gear 56 linked to the slave wire 28 is fitted into the master driving gear 55, but is not fitted into the spur gear 52b. The wires 27 and 28 rotate in opposite directions, and the slave driving gear 56 rotates in the opposite direction to the master driving gear 55.

The mounting tube 46 has a round inner surface and an approximately triangular outer surface in which each corner of an equilateral triangle is curved to be rounded, and openings 46a are formed in three flat portions. Two driving wheels 66 are attached in a rotatable manner to each of the openings 46a. Into the worm gear 52a, the pair of driving wheels 66 are fitted through the opening 46a of the mounting tube 46. When the driving tube 52 rotates, each of the pair of driving wheels 66 rotates about a shaft 66a.

Each of the front wiper 48 and the rear wiper 49 has a sleeve portion that expands in an eave shape to a tip side, and tips of the sleeve portions are in sliding contact with inner circumferential side surfaces when the rotating body 41 moves in a circulating manner.

At a front end of the clamper 50, a regular projection-recess engagement portion is aligned in the circumferential direction. A dedicated jig that is used when the endoscope 2 is mounted is engaged with the projection-recess engagement portion.

The outer unit 45 that is an outside structure of the rotating body 41 has a front bumper 71, a shield cover 72, a cylindrical-shaped support tube 73, and a rear bumper 74. When pressed, the rotating body 41 is received by the front bumper 71 and the rear bumper 74. The shield cover 72 tightly covers the support tube 73.

The front bumper 71 and the rear bumper 74 are fixed to a tip and a rear end of the support tube 73, respectively. In the support tube 73, openings 73a are formed at three spots which are rotationally symmetric at 120 degrees with regard to a central axis thereof. To each of the openings 73a, a roller unit 76 that presses the rotating body 41 toward the driving wheels 66 is attached. The roller unit 76 has two support plates 77, and three driven rollers 78a, 78b, and 78c that are attached in a rotatable manner between the two support plates 77. The driving wheels 66 are arranged between the driven roller 78a and the driven roller 78b and between the driven roller 78b and the driven roller 78c.

The rotating body 41 is pinched between the driving wheels 66 and the driven rollers 78a to 78c. The driving wheels 66 overlap with the respective driven rollers 78a to 78c in the radial direction of the support tube 73, and the rotating body 41 is curved in a wave shape between each of the driven rollers 78a to 78c and the driving wheels 66. A driving unit is configured of the mounting tube 46, the driving tube 52, the support tube 73, each of the driving wheels 66, and each of the driven rollers 78a to 78c.

Figure 6:
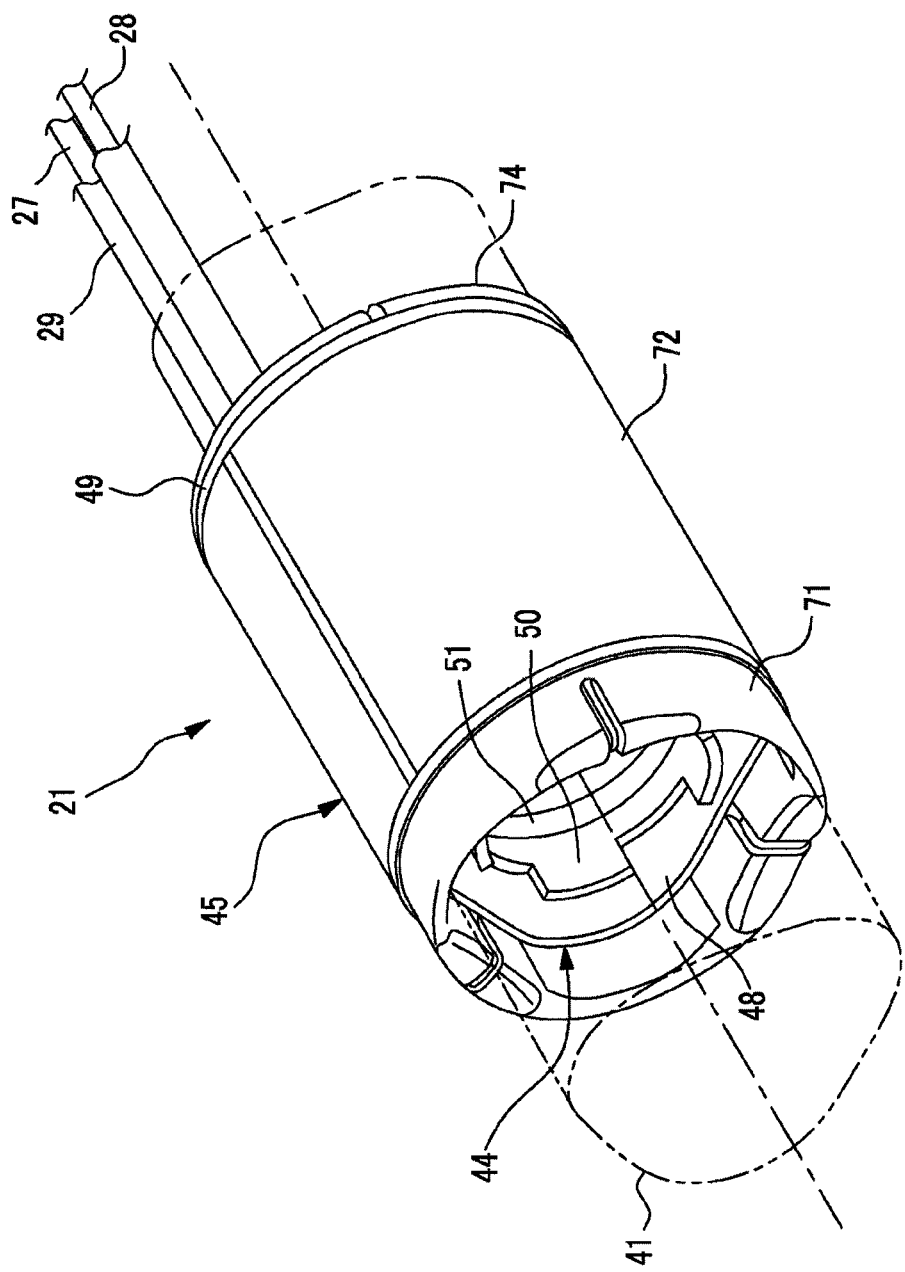
FIG. 6 is a perspective view of the propulsion auxiliary unit.
Figure 7:
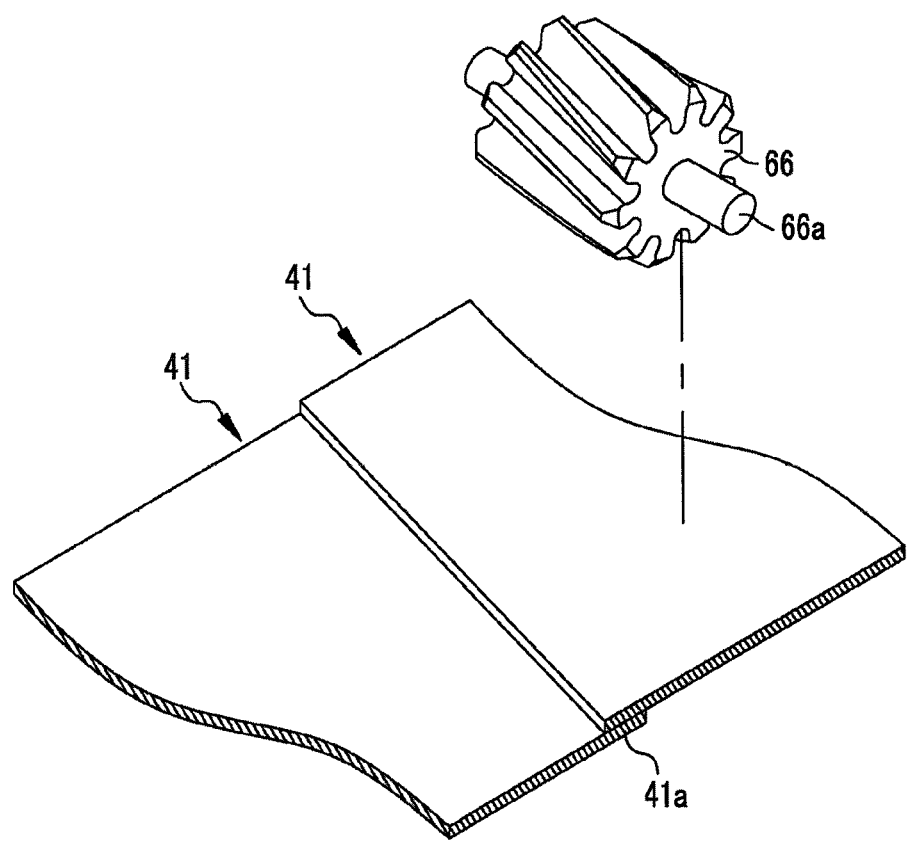
FIG. 7 is a perspective view showing a rotating body and the driving wheel after adhesion.

As shown in FIG. 6, a resin sheet processed into a tubular shape is inserted into the support tube 73 so as to attach the rotating body 41 to the mounting tube 46. Next, a tip and a rear end of the tubular-shaped sheet are folded outside, and the tip and the rear end are reversed so that an inner circumferential surface becomes an outer circumferential surface, and, as shown in FIG. 7, are adhered by contact heat welding or the like in a state where a front end and the rear end overlap with each other. In this manner, the rotating body 41 is formed in a bag shape in which a doughnut is stretched along a hole. Reference numeral 41a is a joint that has a step in which a front end and a rear end of the rotating body 41 overlap with and are adhered to each other.

Figure 8:
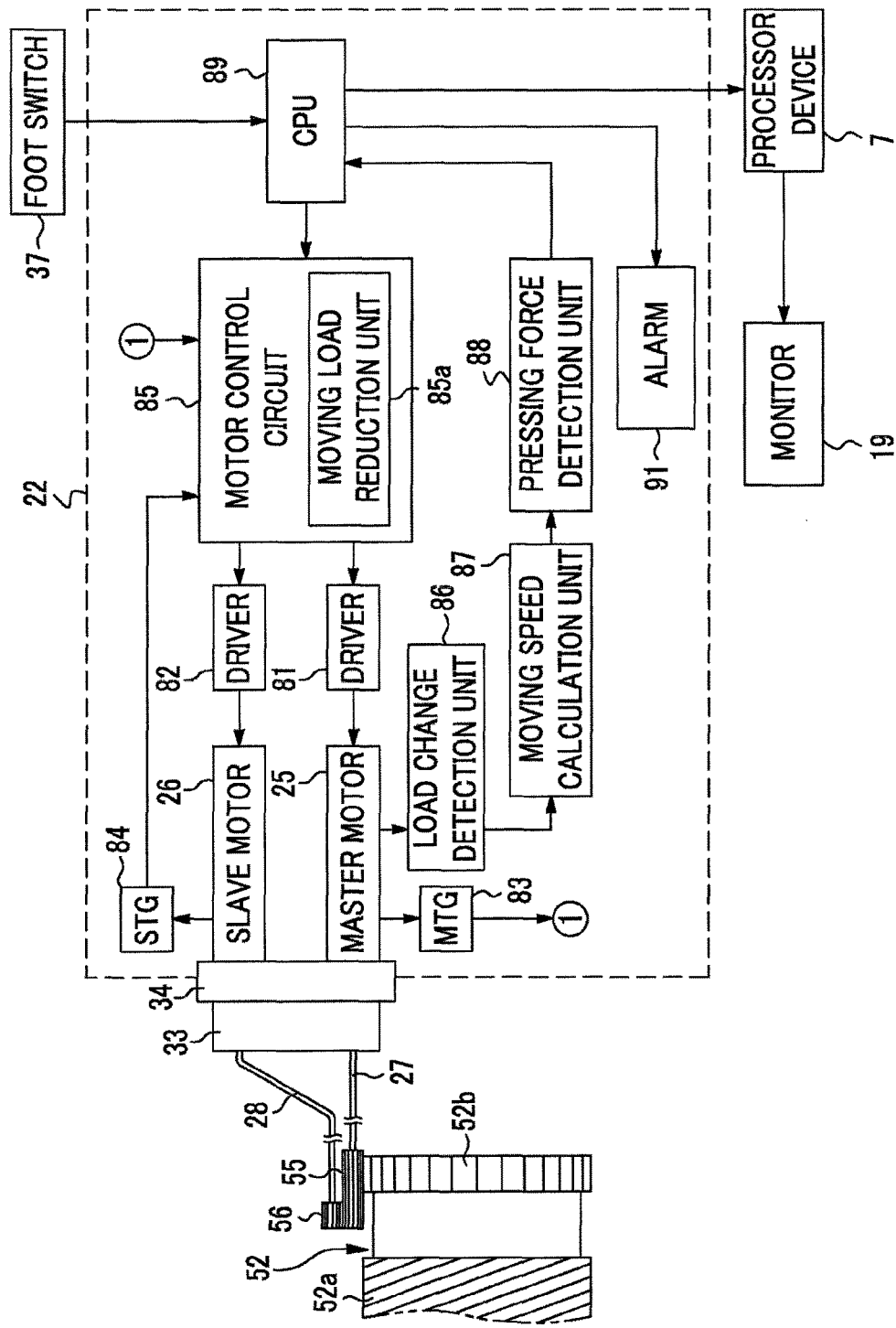
FIG. 8 is a block diagram showing the electrical configuration of an endoscope propulsion auxiliary device.

In FIG. 8, the master motor 25 and the slave motor 26 are disposed in the controller 22. The motors 25 and 26 are, for example, DC motors, and are driven by drivers 81 and 82, respectively. Also, the rotating speed of the motors 25 and 26 are respectively detected by a master tachogenerator (MTG) 83 and a slave tachogenerator (STG) 84, and the obtained rotating speed are sent to a motor control circuit 85 as measured values. In normal control, the motor control circuit 85 controls the rotating speed of the master motor 25 and the slave motor 26 via the drivers 81 and 82 so that the measured values of the rotating speed are maintained as target values.

Figure 9:
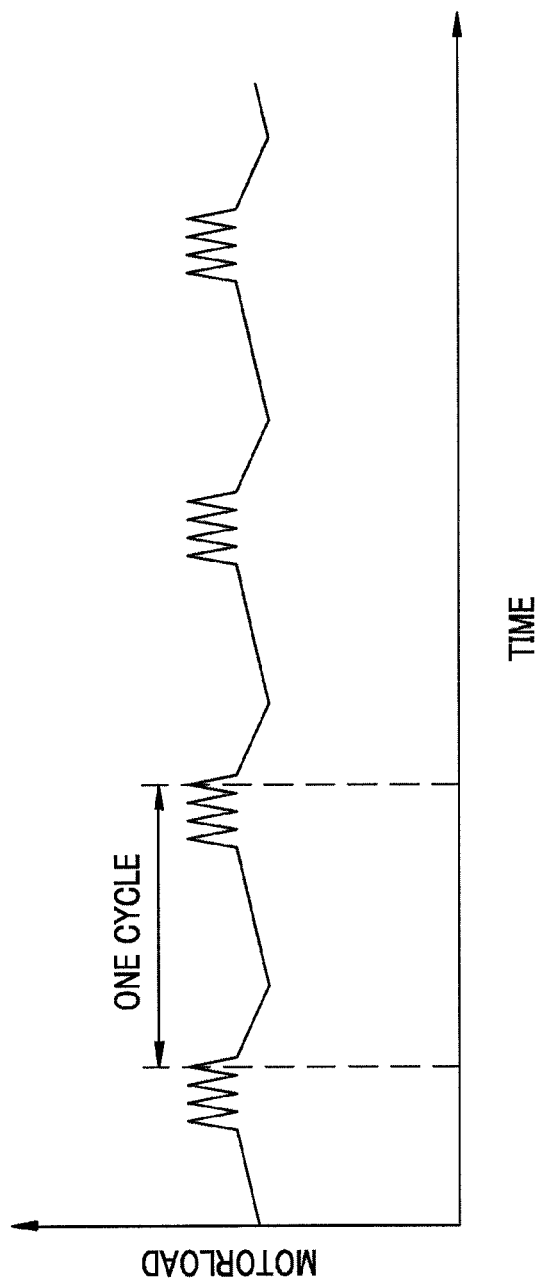
FIG. 9 is a graph showing motor load change.

Transport load increases while the joint 41a (load generation unit) of the rotating body 41 passes through the driving wheels 66 and the driven rollers 78a to 78c. In the embodiment, two driving wheels and three driven rollers are provided. Therefore, as shown in FIG. 9, load change is generated four times by the passing of the joint 41a. When the load change is generated, the voltage or current of the master motor 25 changes. A load change detection unit 86 detects the generation of the load change from the change in the motor current or motor voltage.

A moving speed calculation unit 87 determines the passing of the joint 41a when the load change is generated four times in a row. Then, the time until the next passing of the joint 41a (time of one cycle) is examined. Since the length of the rotating body 41 is already known, the moving speed of the rotating body 41 is calculated by dividing the length by the passing time.

Figure 10:
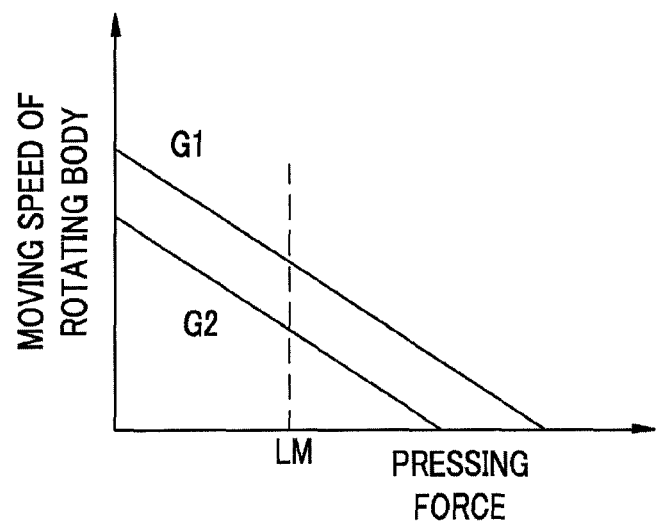
FIG. 10 is a graph showing the relationship between pressing force and rotating body moving speed.

Since in the colon, for example, a boundary between a descending colon and a transverse colon is curved at approximately 90 degrees, a front end portion of the rotating body 41 is pressed against an inner wall of the transverse colon. In this state, the moving load of the rotating body 41 increases, and thus the moving speed decreases. The relationship between the moving speed and the pressing force is shown in FIG. 10. When the motor current is large, the rotating speed of the motor is high. G1 is a characteristic line at the time of supplying the motor current in a normal state, and G2 is a characteristic line in a case where the rotating speed of the motor is decreased to decrease the moving load.

A pressing force detection unit 88 has the characteristic line shown in FIG. 10 as a look-up table, and converts the moving speed to the pressing force referring to the look-up table. The obtained pressing force is sent to a CPU 89. The CPU 89 determines whether the pressing force exceeds a predetermined limit value LM or not. When the pressing force exceeds the predetermined limit value LM, the processor device 7 is notified of the fact, and displays a warning statement onto the monitor 19.

An alarm 91 is disposed in the controller 22, and a warning sound is generated when the pressing force exceeds the predetermined limit value LM. The alarm 91 may draw the attention of the operator by shortening the interval between such warning sounds according to the strength of the pressing force.

The motor control circuit 85 has a moving load reduction unit 85a, and decreases the motor current when the pressing force exceeds the predetermined limit value LM. In this manner, the driving force of the motors 25 and 26 decreases, the rotating speed of the rotating body 41 is slowed down, and the influence on a body wall is suppressed. In this state, the pressing force is obtained by using the characteristic line G2 of FIG. 10.

Next, the effect of the embodiment will be described. The propulsion auxiliary unit 21 is fixed to the endoscope 2. A dedicated jig is used for the fixing, and the clamper 50 is rotated clockwise. The clamper 50 is screwed to a right thread formed on a tip side inner circumference of the mounting tube 46, and thus is moved to a back side (rear end side) by the clockwise rotation to press the C ring 51 on an inclined surface 50a. On a front surface of the C ring 51, an inclined surface inclined as much to a rear end side as to an outer circumferential side is formed, and the inclined surface is pressed by the inclined surface 50a of the clamper 50, and thus the C ring 51 is elastically deformed to have a narrow diameter. When the C ring 51 is deformed, the insertion unit 3 of the endoscope which is inserted into a hollow portion of the mounting tube 46 is tightened to the C ring 51, and the propulsion auxiliary unit 21 is tightly fixed to an outer circumferential surface of the insertion unit 3.

The sheath 29 that is drawn out from a rear end of the propulsion auxiliary unit 21 is stretched to be along a front surface of the insertion unit 3 of the endoscope 2. On a front surface of the sheath 29, marks representing tape stop positions are disposed at appropriate intervals. The sheath 29 is fixed to the insertion unit 3 of the endoscope 2 by matching the marks and using the surgical tape 31. The plug 33 at a rear end of the sheath 29 is inserted into the connector 34 and is connected to the controller 22, and the power of the controller 22 is turned on.

When the power is turned on, the controller 22 electrically checks whether the plug 33 is connected to the connector 34 or not, and a notification is made by using a sound or by flashing a warning light in the case of non-connection or improper connection. In the case of proper connection, a sensor built into the connector 34 reads the model information of the propulsion auxiliary unit 21 from a signal unit that is disposed in a bridge portion of the plug 33. The controller 22 automatically sets a wire rotating speed value according to the model information which is read.

The insertion unit 3 of the endoscope 2 to which the propulsion auxiliary unit 21 is fixed is inserted into the digestive tract, for example, the colon, of a patient. When the foot switch 37 connected to the controller 22 is operated, an instruction is given from the CPU 89 to the motor control circuit 85 so that the rotating speed of the master motor 25 becomes a speed at which the propulsion auxiliary unit 21 is effectively operated, for example, 2,000 rpm. In order to rotate each of the motors 25 and 26 at 2,000 rpm based on the instruction from the CPU 89, the motor control circuit 85 supplies the current according thereto to each of the motors 25 and 26 via the drivers 81 and 82.

The rotating speed data of the master motor 25 and the slave motor 26 detected by the MTG 83 and the STG 84 are input into the motor control circuit 85. The motor control circuit 85 performs feedback control on the current supplied to each of the motors 25 and 26 based on the detected rotating speed so that each of the motors 25 and 26 rotates at a rotating speed which is set.

Each of the motors 25 and 26 is driven by the supply of the current from the motor control circuit 85, and each of the wires 27 and 28 is rotated. The rotation of each of the driving gears 55 and 56 following the rotation of each of the wires 27 and 28 causes the driving tube 52 to rotate via the spur gear 52*b* fitted into the master driving gear 55. The slave driving gear 56 rotates in the opposite direction to the master driving gear 55, and the rotation is transmitted to the master driving gear 55.

When the worm gear 52*a* rotates along with the rotation of the driving tube 52, the driving wheels 66 rotate in the same direction. Between tooth surfaces of the driving wheels 66 and the driven rollers 78*a* to 78*c* of the roller unit 76, the rotating body 41 is strongly pinched. In this manner, the driven rollers 78*a* to 78*c* are driven along with the rotation of the driving wheels 66 and the rotating body 41 pinched by both is moved in the axial direction of the driving tube 52. For example, in FIG. 4, the driven rollers 78*a* to 78*c* rotate counterclockwise when the driving wheels 66 rotate clockwise, and the rotating body 41 pinched thereby is sent to be moved from a rear end side to a tip side on the inner circumferential side (inside the outer unit 45) and the rotating body 41 is sent from the tip side to the rear end side on the outer circumferential side (outside the outer unit 45) of the rotating body 41. In other words, as shown with arrow Y, the toroidal rotating body 41 is moved in a circulating manner to be sent out sequentially from the inner circumferential side to the outer circumferential side at the tip and is retracted sequentially from the outer circumferential side to the inner circumferential side at the rear end.

In a state where the endoscope 2 is inserted into the colon along with the propulsion auxiliary unit 21 and an outer circumferential side surface of the rotating body 41 is in contact with a colon wall, propelling force can be obtained in a direction in which the insertion unit 3 of the endoscope is moved forward or acting force with which the colon wall is pulled toward the operator side can be obtained while the rotating body 41 is moved in a circulating manner.

While the rotating body 41 is moved, foreign substances or the like sticking to the outer circumferential side of the rotating body 41 are moved from the rear end side of the outer unit 45 to the inner circumferential side but, immediately beforehand, the tip of the sleeve portion extending to a rear end side of the rear wiper 49 is in sliding contact with the rotating body 41 to inhibit the drawing in of the foreign substances. Of course, the drawing in of a part of a living tissue along with the movement of the rotating body 41 can be prevented. When the rotating body 41 moves in a circulating manner in the opposite direction, the tip of the sleeve portion of the front wiper 48 achieves the same effect.

The light from the light source device 6 is emitted into the colon through the universal cord 5, the light guide, and the illumination windows 9*a* and 9*b*. The CCD image sensor built into the insertion unit 3 captures an image in the colon and outputs an imaging signal. The imaging signal is input into the processor device 7 via the signal cable and the universal cord 5, and is displayed onto the monitor 19. The operator observes the inner part of the colon through the monitor 19.

In a case where an affected area is found during the observation, a treatment tool suitable for the treatment of the affected area is inserted into the forceps inlet 11 of the endoscope 2 and projects from the forceps outlet 10 to treat the affected area.

The joint 41*a* is formed in the rotating body 41, and, when the joint 41*a* passes between the driving wheels 66 and the driven rollers 78*a* to 78*c*, the load applied to the master motor 25 increases and the load change is generated four times. Based on the cycle of the load change, the moving speed calculation unit 87 calculates the moving speed of the rotating body 41. In this manner, the moving speed of the rotating body 41 can be detected without having to provide the rotating body 41 with a speed detection sensor or the like, and thus space and cost can be saved. Further, sterilization can be facilitated compared to a case where such a sensor is disposed.

The moving speed that is calculated is sent to the pressing force detection unit 88. The pressing force detection unit 88 obtains the pressing force of the rotating body 41 based on the moving speed that is calculated. The pressing force detection unit 88 obtains the pressing force of the rotating body 41 by using the characteristic line G1 of FIG. 10. For example, in a case where the pressing force is 0 (zero) N, the one cycle of the rotating body 41 is 2.5 seconds. In a case where the pressing force is 5 N, slip is generated between the rotating body 41 and the driving wheels 66 and the driven rollers 78*a* to 78*c*, and thus the speed of the rotating body 41 decreases and the one cycle is three seconds.

In a case where the pressing force calculated by the pressing force detection unit 88 exceeds the limit value LM, the CPU 89 instructs the motor control circuit 85 to decrease the motor speed. In this manner, the moving load reduction unit 85*a* of the motor control circuit 85 reduces the current supplied to each of the motors 25 and 26. When the motor current is reduced, the rotating speed of each of the motors 25 and 26 is decreased and the moving speed of the rotating body 41 is decreased. Also, the CPU 89 displays the reduction of the motor speed onto the monitor 19 via the processor device 7. During the decelerated rotation of the motors 25 and 26, the pressing force of the rotating body 41 is obtained by using the characteristic line G2 of FIG. 10. When the pressing force obtained by using the characteristic line G2 of FIG. 10 exceeds the limit value LM, the CPU 89 generates a warning sound by driving the alarm 91. In addition, a warning statement is displayed onto the monitor 19 via the processor device 7. The alarm 91 may sound for a moment before each of the motors 25 and 26 is decelerated.

When the propulsion auxiliary unit 21 is taken out from the insertion unit 3, the clamper 50 is rotated counterclockwise by using a jig. In this manner, the clamper 50 is moved toward the operator while rotating, and releases the pressing on the C ring 51. As a result, the diameter of the C ring 51 expands by the elasticity thereof and the inner circumferential surface is separated from the outer circumferential surface of the insertion unit 3, and the propulsion auxiliary unit 21 can be simply taken out from the endoscope 2.

Figure 11:
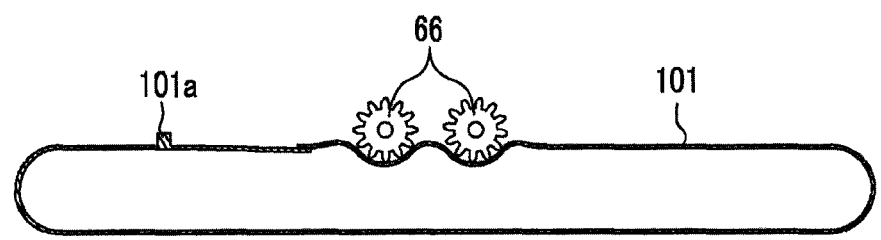
FIG. 11 is a cross-sectional view showing the rotating body that is disposed with a projection and the driving wheel.

In the above-described embodiment, the one cycle of the rotating body is detected by the joint of the rotating body. However, as shown in FIG. 11, a projection 101*a* that is a protruding portion which is larger than the step of the joint may be formed on the rotating body 101. A recessed portion may be formed instead of the projection.

Figure 12:
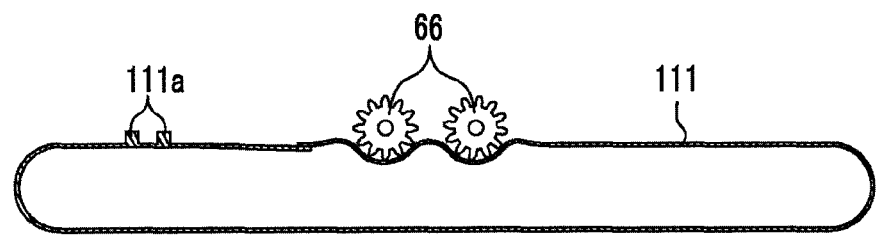
FIG. 12 is a cross-sectional view showing the rotating body where two projections are formed in the moving direction with a predetermined gap being maintained and the driving wheel.

Also, as shown in FIG. 12, a rotating body 111 in which two projections 111*a* are arranged in parallel may be used. In this case, the number of load change increases compared to a case where one joint and one projection are used, and noise identification is ensured.

Figure 13:
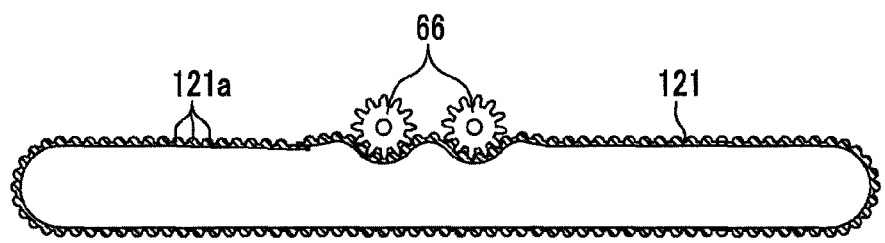
FIG. 13 is a cross-sectional view showing the rotating body where projections are formed on the entire circumference along the moving direction with predetermined gaps and the driving wheel.

Further, as shown in FIG. 13, a rotating body 121 in which projections 121*a* are formed at predetermined pitches over the entire circumference may be used. It is preferable that the projections 121*a* be formed in a gear tooth shape fitted into the driving wheels 66. In this case, the moving speed can be calculated in a short period of time, for example, in a half-circumference or in one-fourths of a circumference, without having to fully rotate the rotating body 121.

Second Embodiment

Figure 14:
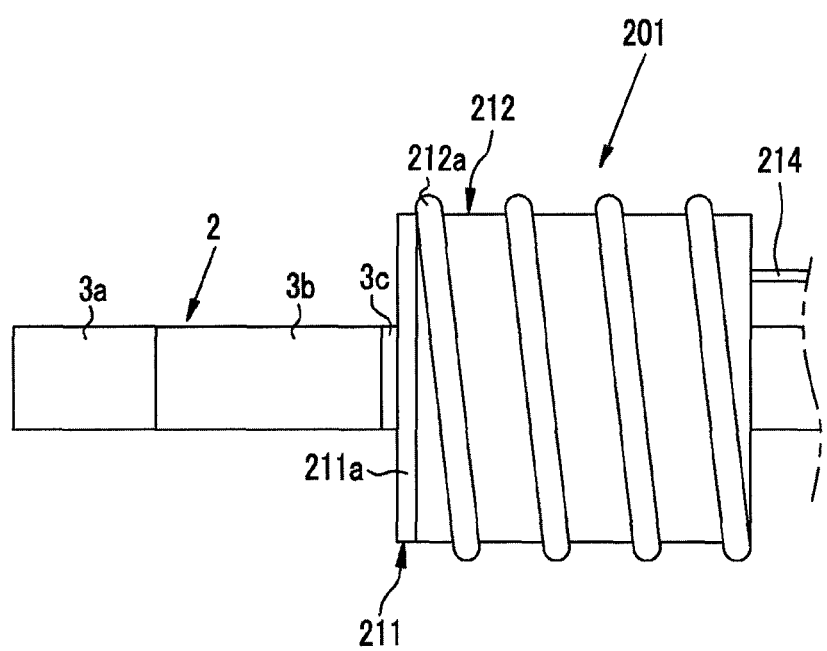
FIG. 14 is a side view showing a propulsion auxiliary unit according to a second embodiment.
Figure 15:
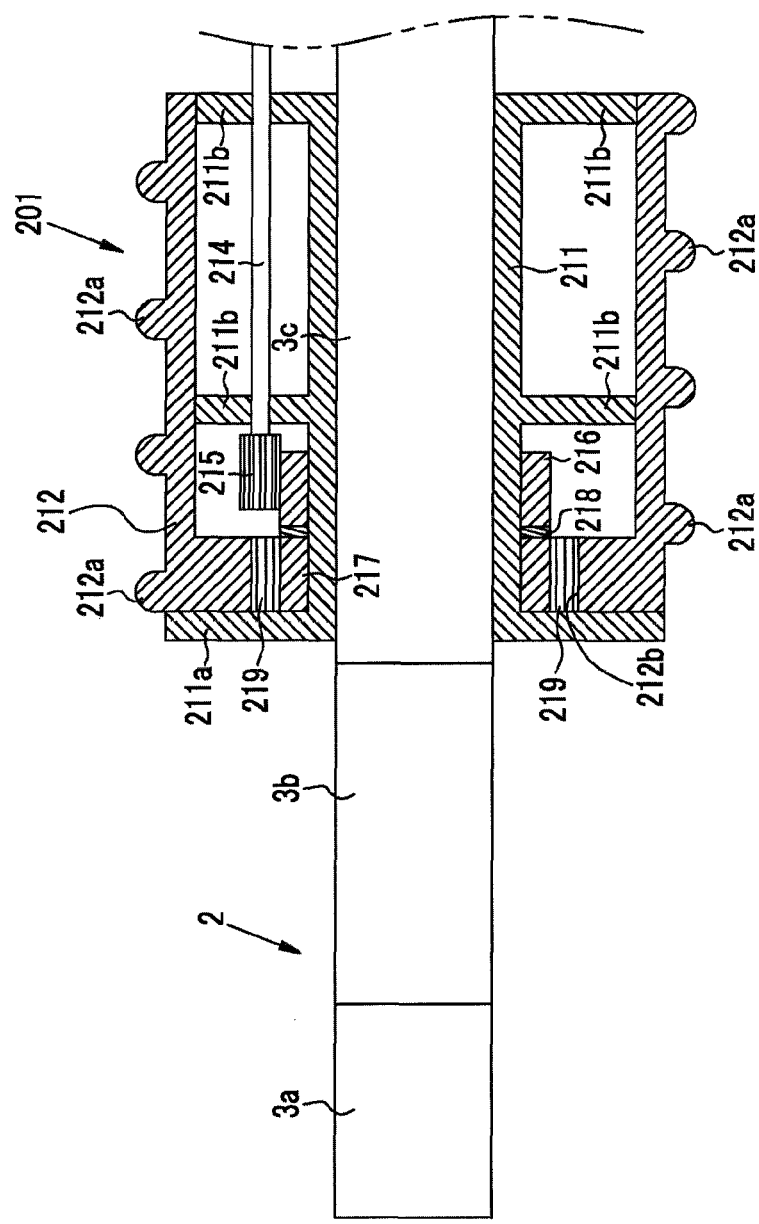
FIG. 15 is a cross-sectional view showing the propulsion auxiliary unit according to the second embodiment.
Figure 16:
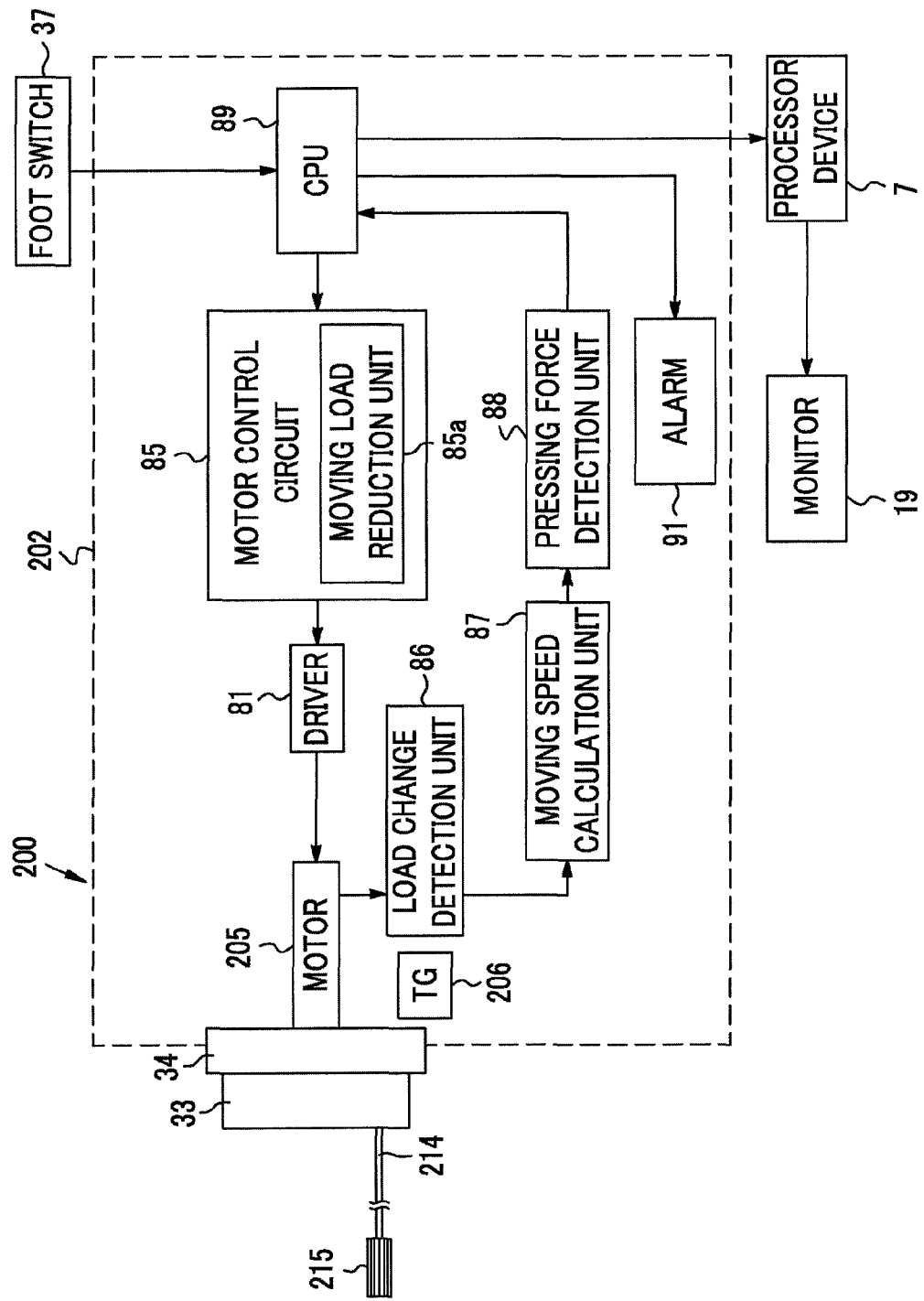
FIG. 16 is a block diagram showing the electrical configuration of an endoscope propulsion auxiliary device according to the second embodiment.

FIGS. 14 to 16 show an endoscope propulsion auxiliary device 200 according to a second embodiment of the present invention. The same reference numerals are used to refer to the same or similar components as in the first embodiment, and detailed description will be omitted.

The endoscope propulsion auxiliary device 200 has a propulsion auxiliary unit 201, and a controller 202. In the controller 202, a motor 205, and a TG 206 that detects the rotating speed of the motor 205 are disposed.

The propulsion auxiliary unit 201 has a fixed tube 211 to which the flexible pipe unit 3c of the endoscope 2 is fixed, and a spiral-shaped driving tube 212 that is supported in a rotatable manner outside the fixed tube 211. Also, the propulsion auxiliary unit 201 has a wire 214 whose one end is connected to the motor 205, a driving gear 215 to which the other end of the wire 214 is connected, a tubular-shaped input side gear 216 that is fitted into the driving gear 215, a tubular-shaped output side gear 217, a clutch 218 formed of rubber or the like that transmits the turning force of the input side gear 216 to the output side gear 217, and idler gears 219 that are fitted into the output side gear 217. The two idler gears 219 are vertically arranged. For the spiral-shaped driving tube 212, a material that has flexibility and elasticity is used.

In the spiral-shaped driving tube 212, a spiral-shaped projection 212a is formed on an outer circumferential surface and a gear 212b is formed on an inner circumferential surface of a tip portion. The idler gear 219 is fitted into the gear 212b. One of the teeth of the gear 212b is a projecting portion that projects from the other teeth.

In the fixed tube 211, a wall portion 211a that prevents the penetration of a liquid from a tip, and support units 211b that support the spiral-shaped driving tube 212 are formed. The number of the support units 211b is two. The wire 214 is inserted into holes formed in the two support units 211b. The wire 214 is inserted into a sheath (not shown). The wire 214, the input side gear 216, and the output side gear 217 may be arranged within the insertion unit 3, and the idler gear 219 may be arranged in an opening portion that is disposed in a part of the insertion unit 3. In this case, only the spiral-shaped driving tube 212 is attached to or detached from the endoscope 2.

When the motor 205 is driven by an instruction from the motor control circuit 85 and the wire 214 is rotated, the driving gear 215 is rotated. By the rotation of the driving gear 215, the spiral-shaped driving tube 212 is rotated via the input side gear 216, the clutch 218, the output side gear 217, and the idler gear 219.

In a state where the endoscope 2 is inserted into the colon with the spiral-shaped driving tube 212 and the spiral-shaped projection 212a of the spiral-shaped driving tube 212 is in contact with the colon wall, propelling force is obtained in a direction in which the insertion unit 3 of the endoscope is moved forward while the spiral-shaped driving tube 212 rotates.

When the projecting portion formed in the gear 212b is fitted into the idler gear 219, load increases and load change is generated. A rotating speed calculation unit 221 calculates the rotating speed of the spiral-shaped driving tube 212 based on the load change. The pressing force detection unit 88 obtains the pressing force of the spiral-shaped driving tube 212 based on the rotating speed that is calculated, and the CPU 89 performs the same control as in the first embodiment based on the pressing force that is obtained.

In the above-described embodiment, when the pressing force exceeds a regulation value, motor driving force is reduced by the moving load reduction unit, a warning is generated by the alarm, and a warning sign is displayed on the monitor, but only one or both thereof may be executed. Also, the generation of a warning sound or the warning sign may be performed when the duration of the state where the pressing force exceeds the regulation value is longer than a predetermined time.

Also, in the above-described embodiment, the CPU reduces the moving speed of the rotating body in a case where the pressing force that is calculated exceeds a set value. However, the driving of the motor may be stopped and the rotation of the rotating body may be stopped.

Further, the pressing force of the rotating body may be directly calculated based on the moving cycle of the rotating body without having to calculate the moving speed of the rotating body. Furthermore, the pressing force of the rotating body may be calculated by using both of the moving cycle or the moving speed of the rotating body and a torque signal value.

Also, in the above-described embodiment, the propulsion of the endoscope is assisted by the rotating body that covers the support tube over the entire circumference, but the propulsion of the endoscope may be assisted by a plurality of endless belts covering a part of the circumferential direction of the support tube.

Also, the present invention can be used in medical apparatuses other than the endoscope if inserted into the body.

What is claimed is:

1. A medical drive device comprising:
   a spiral-shaped driven unit that is capable of attaching to a part of an endoscope and is rotatable around an axis of the endoscope;
   a gear structure in which a plurality of gears are meshed so that a driving force transmission path transmitting a driving force between the spiral-shaped driven unit and the gear structure is provided, said gear structure moving the spiral-shaped driven unit in a circulating manner by the driving of a motor;
   a load generation unit that is formed at the driving force transmission path, and the load generation unit changes a physical load applied to the gear structure when the gear structure moves the spiral-shaped driven unit, in each cycle of a movement of the spiral-shaped driven unit in the circulating manner; and
   a processor configured to detect a pressing force of the spiral-shaped driven unit based on the timings of generation of the physical load change by the load generation unit.

2. The medical drive device according to claim 1, wherein the processor detects the pressing force of the spiral-shaped driven unit based on the rotating speed of the spiral-shaped driven unit.

3. The medical drive device according to claim 2, wherein the gear structure has a wire whose one end is connected to the motor, a driving gear to which the other end of the wire is connected, a tubular-shaped input side gear that is fitted into the driving gear, a tubular-shaped output side gear, a clutch that transmits the turning force of the input side gear to the output side gear and idler gears that are fitted into the output side gear.

4. The medical drive device according to claim 2,
wherein the load generation unit is provided at one of the plurality of gears and the load generation unit is a projecting portion that projects from other teeth of the gear.

5. The medical drive device according to claim 1,
wherein the processor detects the pressing force of the spiral-shaped driven unit based on the moving cycle of the spiral-shaped driven unit.

6. The medical drive device according to claim 5,
wherein the gear structure has a wire whose one end is connected to the motor, a driving gear to which the other end of the wire is connected, a tubular-shaped input side gear that is fitted into the driving gear, a tubular-shaped output side gear, a clutch that transmits the turning force of the input side gear to the output side gear and idler gears that are fitted into the output side gear.

7. The medical drive device according to claim 5,
wherein the load generation unit is provided at one of the plurality of gears and the load generation unit is a projecting portion that projects from other teeth of the gear.

8. The medical drive device according to claim 1,
wherein the processor detects the pressing force of the spiral-shaped driven unit based on both of the moving cycle of the spiral-shaped driven unit or the moving speed of the spiral-shaped driven unit and a torque signal value of the motor.

9. The medical drive device according to claim 1,
wherein the gear structure has a wire whose one end is connected to the motor, a driving gear to which the other end of the wire is connected, a tubular-shaped input side gear that is fitted into the driving gear, a tubular-shaped output side gear, a clutch that transmits the turning force of the input side gear to the output side gear and idler gears that are fitted into the output side gear.

10. The medical drive device according to claim 1,
wherein the load generation unit is provided at one of the plurality of gears and the load generation unit is a projecting portion that projects from other teeth of the gear.

11. The medical drive device according to claim 1, further comprising
a motor control circuit that reduces the physical load applied to the spiral-shaped driven unit when the pressing force exceeds a predetermined value.

12. The medical drive device according to claim 11,
wherein the motor control circuit reduces the rotating speed of the motor.

13. The medical drive device according to claim 1, further comprising
a display unit that displays the strength of the pressing force exceeding the predetermined value.

14. The medical drive device according to claim 13,
wherein the display unit is an alarm that generates a warning sound.

15. The medical drive device according to claim 13,
wherein the display unit is an alarm that generates a sound at an interval according to the strength of the pressing force.

16. The medical drive device according to claim 13,
wherein the display unit is a monitor that displays an endoscope image.

* * * * *